United States Patent [19]

Baldi

[11] Patent Number: 4,965,095

[45] Date of Patent: Oct. 23, 1990

[54] METHOD FOR REFURBISHING USED JET ENGINE HOT SECTION AIRFOILS

[75] Inventor: Alfonso L. Baldi, Wynnewood, Pa.

[73] Assignee: Alloy Surfaces Company, Inc., Wilmington, Del.

[21] Appl. No.: 289,595

[22] Filed: Dec. 22, 1988

Related U.S. Application Data

[63] Continuation-in-part of Ser. No. 205,387, Jun. 10, 1988, Pat. No. 4,895,609, and a continuation-in-part of Ser. No. 182,718, Apr. 18, 1988, abandoned, and a continuation-in-part of Ser. No. 862,712, May 13, 1986, Pat. No. 4,871,708, and a continuation-in-part of Ser. No. 830,767, Feb. 19, 1986, Pat. No. 4,799,799, and a continuation-in-part of Ser. No. 757,606, Jul. 22, 1985, abandoned, and a continuation-in-part of Ser. No. 707,606, Mar. 4, 1985, Pat. No. 4,824,482, and a continuation-in-part of Ser. No. 685,910, Dec. 27, 1984, Pat. No. 4,820,362, and a continuation-in-part of Ser. No. 584,538, Feb. 28, 1984, Pat. No. 4,845,139, and a continuation-in-part of Ser. No. 538,541, Oct. 3, 1983, Pat. No. 4,830,931, and a continuation-in-part of Ser. No. 479,211, Mar. 28, 1983, Pat. No. 4,476,244, which is a continuation of Ser. No. 632,016, Jul. 18, 1984, abandoned, which is a continuation of Ser. No. 605,248, Apr. 30, 1984, abandoned, which is a continuation of Ser. No. 571,510, Jan. 17, 1984, Pat. No. 4,537,927, which is a continuation of Ser. No. 488,103, Apr. 25, 1983, Pat. No. 4,615,920, which is a continuation of Ser. No. 417,214, Sep. 13, 1982, abandoned, which is a continuation of Ser. No. 398,850, Jul. 16, 1982, Pat. No. 4,467,016, which is a continuation of Ser. No. 302,979, Sep. 17, 1981, abandoned, which is a continuation of Ser. No. 281,405, Jul. 8, 1981, Pat. No. 4,708,913, which is a continuation of Ser. No. 230,333, Feb. 2, 1981, Pat. No. 4,347,267, which is a continuation of Ser. No. 191,780, Sep. 29, 1980, abandoned, which is a continuation of Ser. No. 172,671, Jul. 28, 1980, Pat. No. 4,435,481, which is a continuation of Ser. No. 73,539, Sep. 7, 1979, Pat. No. 4,260,654.

[51] Int. Cl.$^5$ ............................................. B32B 35/00
[52] U.S. Cl. ........................................ 427/142; 134/2; 427/252; 427/328; 427/343
[58] Field of Search ............... 427/309, 252, 320, 336, 427/328, 329, 343, 142, 349; 134/3, 2, 41

[56] References Cited

U.S. PATENT DOCUMENTS

| 2,561,565 | 7/1951 | Edson et al. | 228/219 |
| 2,561,566 | 7/1951 | Edson et al. | 228/219 |
| 2,571,328 | 10/1951 | Baker | 51/281 R |
| 2,585,819 | 2/1952 | Moore et al. | 228/219 |
| 2,851,387 | 9/1958 | Low | 148/16.6 |
| 3,197,341 | 7/1965 | Wallace | 134/3 |
| 3,276,903 | 10/1966 | Galmiche et al. | 427/253 |

(List continued on next page.)

FOREIGN PATENT DOCUMENTS 1454217  11/1976  United Kingdom .

OTHER PUBLICATIONS

Genieys, "Brazing in Reducing Fluoride-Containing Atmosphere", The British Association for Brazing and Soldering First International Brazing & Soldering Conference, Nov. 1972.

Parmentier et al, "Brazing Stainless Steel in a Stable Reducing Atmosphere of Fluoride", Welding Journal pp. 15-22, Nov. 1977.

Primary Examiner—Sadie Childs
Attorney, Agent, or Firm—Connolly & Hutz

[57] ABSTRACT

Workpieces are very rapidly diffusion coated by heating the packed workpiece at a rate that brings the workpiece to diffusion-coating temperature and then completing the diffusion coating, all in less than 50 minutes, then cooling. Workpiece can have top coating layer of aluminum flake covered by a layer of extremely fine alumina or silica in a magnesium chromate binder, to provide surface having roughness at least about 10 micro-inches smoother than before the top coating. Used aluminized jet engine hot section members can be reconditioned by a fluoridizing treatment that deoxidizes and also removes residual aluminizing, so that the members can then be repaired if necessary and re-aluminized.

2 Claims, 1 Drawing Sheet

U.S. PATENT DOCUMENTS

| | | | |
|---|---|---|---|
| 3,458,353 | 7/1969 | Baldi | 134/3 |
| 3,622,391 | 11/1971 | Baldi | 134/3 |
| 3,677,789 | 7/1972 | Bumgardt et al. | 427/250 |
| 3,713,206 | 1/1973 | Galmiche et al. | 428/556 |
| 3,801,357 | 4/1974 | Baldi | 427/253 |
| 4,098,450 | 7/1978 | Keller et al. | 228/119 |
| 4,132,816 | 1/1979 | Benden et al. | 427/237 |
| 4,141,760 | 2/1979 | Baldi | 428/556 |
| 4,188,237 | 2/1980 | Chasteen | 134/2 |
| 4,324,594 | 4/1982 | Chasteen | 134/2 |
| 4,327,134 | 4/1982 | Baldi | 427/253 |
| 4,328,044 | 5/1982 | Chasteen | 134/2 |
| 4,347,267 | 8/1982 | Baldi | 427/252 |
| 4,400,289 | 8/1983 | Geldner et al. | 134/3 |
| 4,405,379 | 9/1983 | Chasteen | 134/2 |

METHOD FOR REFURBISHING USED JET ENGINE HOT SECTION AIRFOILS

This application is a continuation-in-part of Ser. No. 205,387 filed June 10, 1988, U.S. Pat. No. 4,895,609 granted Jan. 23, 1990, Ser. No. 182,718 filed Apr. 18, 1988, Ser. No. 862,712 filed May 13, 1986, U.S. Pat. No. 4,871,708 granted Oct. 3, 1989, Ser. No. 830,767 filed Feb. 19, 1986 (U.S. Pat. No. 4,799,979 granted Jan. 24, 1989), Ser. No. 777,755 filed Sept. 19, 1985 (subsequently abandoned), Ser. No. 757,606 filed July 22, 1985 (subsequently abandoned), Ser. No. 707,656 filed Mar. 4, 1985 (U.S. Pat. No. 4,824,482 granted Apr. 25, 1989), Ser. No. 685,910 filed Dec. 27, 1984 (U.S. Pat. No. 4,820,362 granted Apr. 11, 1989), Ser. No. 584,538 filed Feb. 28, 1984 (U.S. Pat. No. 4,845,139 granted July 4, 1989), Ser. No. 538,541 filed Oct. 3, 1983, U.S. Pat. No. 4,830,931, granted May 16, 1989, and Ser. No. 479,211 filed Mar. 28, 1983, U.S. Pat. No. 4,897,375, granted Jan. 30, 1990 which parent applications are in turn continuations-in-part of Ser. No. 632,016, filed July 18, 1984 and subsequently abandon, Ser. No. 605,248 filed Apr. 30, 1984 and subsequently abandoned, Ser. No. 571,510 filed Jan. 17, 1984 (U.S. Pat. No. 4,537,927 granted Aug. 27, 1985), Ser. No. 488,103 filed Apr. 25, 1983 (Patent No. 4,615,920 granted Oct. 7, 1986), Ser. No. 417,214 filed Sept. 13, 1982 (subsequently abandoned), Ser. No. 398,830 filed July 16, 1982 (U.S. Pat. No. 4,467,016 granted Aug. 21, 1984), Ser. No. 302,979 filed Sept. 17, 1981 (subsequently abandoned), Ser. No. 281,405 filed July 8, 1981 (U.S. Pat. No. 4,708,913 granted Nov. 24, 1987), Ser. No. 230,333 filed Feb. 2, 1981 (U.S. Pat. No. 4,347,267 granted Aug. 31, 1982), Ser. No. 191,780 filed Sept. 29, 1980 (subsequently abandoned), Ser. No. 172,671 filed July 28, 1980 (U.S. Pat. No. 4,435,481 granted Mar. 6, 1984) and Ser. No. 73,539 filed Sept. 7, 1979 (U.S. Pat. No. 4,260,654 granted Apr. 17, 1981).

The present invention relates to the diffusion coating of metals and related operations.

Additional objects of the present invention include the provision of pyrophoric products.

The foregoing as well as still further objects of the present invention will be more fully understood from the following description of several of its exemplifications, reference being made to the accompanying drawing which is a vertical sectional view of a set-up for cleaning a workpiece to be diffusion coated in accordance with the present invention.

Aluminizing of ferrous metals is widely practiced inasmuch as such treatment sharply increases the resistance of these metals to corrosion. Even stainless steels can have their corrosion resistance increased in this manner, and stainless steel gas turbine engines have long had their compressor blades diffusion aluminized to this end. U.S. Pat. Nos. 3,859,061 and 3,597,172 describe such an operation.

The aluminizing operation adds some thickness to the metal workpiece that is aluminized, and to keep the dimensional changes small the aluminizing is effected by diffusion, generally pack diffusion, as described in U.S. Pat. No. 3,859,061. Thus, the industry generally calls for an aluminized case only about 0.2 to about 2 mils thick. Such cases increase the overall metal thickness only about 0.15 to about 1.5 mil—that is, about ½ to ¾ the thickness of the case itself. They also provide considerable corrosion protection even though their maximum aluminum content, at the outer stratum for instance, is about 50% or below.

Aluminizing a workpiece by dipping it into molten aluminum is not suitable for such purposes because it adds too much thickness as well as too much irregularity, and the outer stratum thus formed is entirely or almost entirely aluminum which does not have the strength or hardness of a ferrous metal. Gas turbine engine airfoils are designed to have the minimum dimensions that provide the desired strength, and some can have an overall thickness of less than 50 mils. Adding 2 mils to each face of such a small thickness takes the airfoil out of tolerance, and manufacturing the airfoil thinner to accommodate such heavy aluminizing weakens the airfoil excessively.

Such small airfoils not only have very close dimensional tolerances, but they are fitted very close to each other so that the gases being compressed by them have a very narrow path to move through. These gases also move at very high speed through the narrow paths, and it is accordingly very important that the airfoil surfaces defining the paths be quite smooth. In some cases a smoothness of about 25 micro-inches is needed, although as much as 38 micro-inches can generally be tolerated.

Unfortunately the low-temperature diffusion aluminizing of age-hardenable stainless steels widely used in the foregoing airfoils causes their surfaces to become excessively rough. Thus, such an airfoil which before aluminizing can have an 18 micro-inch roughness, becomes an aluminized airfoil with a roughness of 40 or more micro-inches. Similar roughening takes place when diffusion aluminizing workpieces containing other age-hardenable stainless steels such as 17-4 PH and those containing about 2 to 5% molybdenum.

It is not practical to try to smooth the surfaces after they have become roughened this way. For one thing, any removal of surface metal by polishing reduces the thickness of the aluminized case and thus reduces the protection that the aluminizing was intended for.

Aluminizing at high temperatures, that is about 1200° F., causes less roughening, but is not desired inasmuch as the aluminizing is generally the last treatment of the workpiece at high temperatures, and aluminizing at a temperature above about 950° F. genrally leaves the workpiece in need of additional heat treatment to improve its mechanical properties.

Excessive roughening during low-temperature diffusion aluminizing is avoided without significantly detracting from the properties of the aluminized product, by preceding the aluminizing with the deposit on the surface to be aluminized, of a layer of nickel or cobalt or mixtures of the two, not over about 0.1 mil thick. This is shown in parent Ser. No. 73,539, the contents of which are hereby incorporated herein as though fully set forth.

The aluminized blades or other airfoils can be used with or without the top coatings described in U.S. Pat. Nos. 3,859,061, 3,958,046, 3,948,687, 3,764,371 and 4,141,760 as well as parent applications Ser. Nos. 417,214 and 632,016. After drying and firing, these top coatings generally provide a surface somewhat smoother than that of the surface on which they are applied. Thus, a top coating containing leafing aluminum as described in column 6 of U.S. Pat. No. 3,958,046, applied as a 0.3 milligram per square centimeter layer over the aluminized product of Example 1 in the present specification and fired at 700° F., improves the smoothness by about 2 to 5 micro-inches. Such a top coating over a rougher similarly aluminized workpiece which did not have the thin nickel electroplate, brought the top smoothness down to close to 30 micro-inches.

Burnishing the coatings by agitating the coated workpieces in a burnishing barrel with steel burnishing discs as disclosed in Ser. No. 417,214 further improves the top smoothness, and the contents of that application are incorporated herein as though fully set out.

Increasing the number of top coating layers on the workpiece further improves the smoothness, but will generally not get the smoothness much below about 24 micro-inches. A series of three layers of the above-noted flake aluminum coating on the product of Example 4 builds up the total top coating weight to 0.8 to 0.9 milligrams per square centimeter and shows a surface roughness as low as about 10 to 20 micro-inches.

Some top coating formulations when cured form hydrophobic surfaces over which it is difficult or impossible to apply a uniform overlying layer. The teflon-containing formulations of U.S. Pat. No. 3,948,687 are examples of such difficult materials. However, top coatings that contain at least about 5% leafing aluminum by weight, or contain at least about 0.1% by weight wetting agent not destroyed or driven off by a curing operation, will accept overlying coatings fairly well.

One type of coating seems unique in that when applied over a top coating containing flake aluminum, has an exceptional smoothing effect. Thus, an aqueous dispersion of colloidal silica containing 14% of the silica, and also containing 15% of a bonding agent such as magnesium chromate or mixtures of magnesium phosphate and magnesium chromate or such mixtures that also contain a little free phosphoric or chromic acid, when applied over other top coatings or other layers of the same top coating, will get the smoothness down to 10 to 15 micro-inches. Such a smoothness does not appear obtainable from other top coating layers regardless of how many are applied.

Thus, an improvement of 14 micro-inches is obtained when coating an unaluminized Type 304 stainless steel compressor blade having an original roughness of 42 micor-inches after glass bead blasting to clean it, using the following coating treatment:

EXAMPLE 1

(a) Spray on the blade surface a suspension of the aluminum paste of Example I in U.S. Pat. No. 3,318,716 dispersed in 30 times its weight of a 4% water solution of $MgCrO_4$, the coating residue after drying weighing about 0.25 milligrams per square centimeter.

(b) Dry and then bake the coated blade at 700° F. to 800° F. for ten minutes.

(c) Repeat steps (a) and (b) on the baked blade.

(d) Repeat steps (a) and (b) again.

(e) Spray on the resulting coated blade a 5% suspension of colloidal alumina in the teflon-free magnesium phosphate-chromate acid solution of Example II in U.S. Pat. No. 3,948,687, the alumina particles having a particle size below 10 millimicrons, to leave a stratum that after drying weighs about 0.6 milligrams per square centimeter.

(f) Repeat the drying and baking step (b).

(g) Repeat step (e) on the thus-baked blade.

(h) Repeat the drying and baking.

(i) Repeat step (e) again.

(j) Repeat the drying and baking.

The final coated blade shows a roughness of about 28 micro-inches and makes a very effective compressor blade for jet engines.

This exceptional top smoothness is provided by dispersions containing about 1% to 20% of silica or alumina particles no larger than about 25 millimicrons in size and a water-soluble bonding agent in an amount at least equal to that of the dispersed particles. However, magnesium chromate is a particularly desirable bonding agent inasmuch as it has strong corrosion-inhibiting effects on a metal workpiece it covers. As much as half the magnesium chromate can be replaced by magnesium phosphate and/or chromic acid and/or phosphoric acid. The hardness and mar-resistance of aluminum flake coatings is also markedly increased by such colloidal over-coatings.

The foregoing smoothing effect of top coatings is provided on other substrates such as on type 410 stainless steel airfoils that have been aluminized without the help of the thin nickel or cobalt flash electroplate, but such electroplates at least 0.01 mil thick make for a much smoother product on age-hardenable stainless steels.

The compositions of AM 355 as well as of other typical age-hardenable steels suitable for the present invention follows, taken from ASTM Data Series Publication No. DS 9d, October 1967.

| GROUP I FERRITIC (MARTENSITIC) STEELS | | | | | | | | | | | | | | |
|---|---|---|---|---|---|---|---|---|---|---|---|---|---|---|
| Nominal Chemical Compositions, percent | | | | | | | | | | | | | | |
| Alloy | C | Mn | Si | Cr | Ni | Co | Mo | W | Cb | Ti | Al | B | Zr | Fe | Other |
| Age-Hardening Stainless Steels | | | | | | | | | | | | | | |
| AM-350 | 0.10 | 1.00 | 0.40 | 16.50 | 4.25 | — | 2.75 | — | — | — | — | — | — | Bal. | — |
| AM-350 | — | — | — | — | — | — | — | — | — | — | — | — | — | — | — |
| AM-355 | 0.15 | 1.00 | 0.40 | 15.50 | 4.25 | — | 2.75 | — | — | — | — | — | — | Bal. | 0.10 N |
| AM-355 | — | — | — | — | — | — | — | — | — | — | — | — | — | — | — |
| AM-363 | 0.04 | 0.15 | 0.05 | 11.00 | 4.00 | — | — | — | — | 0.25 | — | — | — | Bal. | — |
| 15-5PH | 0.04 | 0.30 | 0.40 | 15.00 | 4.60 | — | — | — | 0.25 | — | — | — | — | Bal. | 3.30 Cu |
| 17-4PH | 0.04 | 0.30 | 0.60 | 16.00 | 4.25 | — | — | — | 0.25 | — | — | — | — | Bal. | 3.30 Cu |
| 17-7PH | 0.07 | 0.50 | 0.30 | 17.00 | 7.10 | — | — | — | — | — | 1.10 | — | — | Bal. | — |
| 17-7PH | — | — | — | — | — | — | — | — | — | — | — | — | — | — | — |
| PH13-8 Mo | 0.04 | 0.05 | 0.05 | 12.75 | 8.10 | — | 2.2 | — | — | — | 1.10 | — | — | Bal. | — |
| PH14-8 Mo | 0.04 | 0.30 | 0.40 | 14.35 | 8.15 | — | 2.2 | — | — | — | 1.10 | — | — | Bal. | — |
| PH15-7 Mo | 0.07 | 0.50 | 0.30 | 15.10 | 7.10 | — | 2.2 | — | — | — | 1.10 | — | — | Bal. | — |
| Pyromet X-15 | 0.03 | 0.10 | 0.10 | 15.00 | — | 20 | 3.0 | — | — | — | — | — | — | Bal. | — |
| AFC-77 | 0.15 | — | — | 14.50 | — | 13 | 5.0 | — | — | — | — | — | — | Bal. | 0.40 V |
| Stainless W | 0.12 | — | — | 17.00 | 7.00 | — | — | — | — | $1.0^a$ | $1.0^a$ | — | — | Bal. | 0.2 N |
| Illium P | 0.20 | 0.75 | 0.75 | 28.00 | 8.00 | — | 2.25 | — | — | — | — | — | — | 56.8 | 3.25 Cu |

-continued

| GROUP I FERRITIC (MARTENSITIC) STEELS | | | | | | | | | | | | | | |
|---|---|---|---|---|---|---|---|---|---|---|---|---|---|---|
| Nominal Chemical Compositions, percent | | | | | | | | | | | | | | |
| Alloy | C | Mn | Si | Cr | Ni | Co | Mo | W | Cb | Ti | Al | B | Zr | Fe | Other |
| Illium PD | 0.10 | 0.75 | 0.75 | 26.00 | 5.00 | 6.5 | 2.25 | — | — | — | — | — | — | 58.0 | — |

[a] For rupture in 100 and 1000 hr. Not for design purposes.
[b] Cast alloy.
[c] Maximum.
[d] Experimental alloy.
[e] Alloy known not to be in commercial production.

Other suitable top coatings are those described in parent Ser. No. 632,016, the contents of which are hereby incorporated herein as though fully set out. The coating of Example IX of that application is particularly suited for application to jet engine compressor blades without a prior aluminizing.

When a stainless steel workpiece is to be aluminized, a very effective pre-cleaning is accomplished by the following sequence, or by grit blasting with 220 mesh alumina grit.

EXAMPLE 2

First, subject the workpiece to ½ minute cathodic treatment at about 50 amperes per square foot in a 10% solution of sodium carbonate in water, then anodically treat it in the same solution at about the same current density for about the same time, after which the workpiece is rinsed with water, dipped in cold concentrated Hcl diluted with water, followed by another water rinse.

The resulting cleaned workpiece with a surface roughness of about 18 micro-inches is ready for plating in an acid nickel salt bath to a pick-up of about ½ milligram per square centimeter producing a nickel flash about 0.07 mil thick. After rinsing and drying, it can then be aluminized as in parent Ser. No. 73,539 for 30 hours at 870° F. to 890° F. to yield an aluminized case about 0.7 mil thick and having a surface roughness of about 22 to 23 micro-inches.

Diffusion coating at temperatures no higher than about 1000° F., as in the aluminizing of Ser. No. 73,539 is readily accomplished in short periods of time—not over 45 minutes of heating is generally needed to bring the workpieces to temperature and obtain an aluminized case at least 1 mil thick. Thinner cases require only about 30 minutes or even less. Zinc and aluminum can both be very effectively and very rapidly diffusion coated into other metals at the foregoing low temperatures.

To further save time, the retort cooling is best effected by withdrawing it from the furnace in which the heating is carried out. Exposed to the ambient air and with the help of the flushing gas stream between retorts, the retort assembly cools in about 15 minutes to the point that the outer retort can be opened and the inner retort withdrawn, exposed to the atmosphere and emptied. In this way the entire diffusion coating sequence, including the completion of the cool-down, takes only about an hour or 65 minutes. This compares with the 1 hours disclosed in U.S. Pat. No. 3,824,122 for just the heating time. The cool-down down can also be accelerated by blowing air over the cooling retort assembly or by lowering it into a quenching liquid such as water.

U.S. Pat. No. 3,117,846 suggests a powder pack diffusion heating for ½ hour, but that time does not include the time needed to bring the powder pack and the workpiece to the diffusion coating temperature. Such heat-up time is generally a number of hours if the continuous treatment technique of U.S. Pat. No. 3,824,122 is not used.

Pack chromizing is generally not conducted at temperatures below about 1100° F., so that it cannot be completed as rapidly as the most rapid pack aluminizing. However, a 300° F. or 400° F. increase in diffusing temperature only takes about five minutes longer to attain by vigorous heat-up.

Diffusion coating to catalytically activate the surface of a metal foam, such as nickel foam described in U.S. Pat. 3,111,396, is particularly desirable inasmuch as such a foam presents a very large metal surface and does not have a fragility of thin foil or screening. The diffusion-coating treatment generally introduces into the surface of the metal being activated a relatively high concentration of an embrittling metal such as aluminum, and fragile shapes such as foil and thin screening tend to break unless very carefully handled during this treatment.

The catalytic activation of platinum and other metals of the platinum family is preferably applied to very thin substrates in the interest of reducing the amount of such expensive metals needed, and here also a metal foam shape as described in U.S. Pat. No. 3,111,396 is desirable.

As described in Ser. No. 632,016, foils can be catalytically and pyrophorically activated by aluminizing followed by leaching, all on a continuous basis. Thus, a long length of steel foil can be unwound from a supply reel, subjected to the activation, and then wound up on a take-up reel with the entire activation sequence taking less than thirty minutes.

The first step in the activation sequence is preferably a surface cleaning as by blasting with glass beads or fine sand and/or electrolytic or non-electrolytic cleaning. Heating of the foil can be initiated as it is unreeled and before, during or immediately after the cleaning step. The heating is then continued as the moving foil goes through a diffusion aluminizing by spray coating with molten aluminum as it heats up to 1450° F., and is then held at that temperature for about ten to forty minutes. Doing the diffusion at 1450° F. takes at least about twenty minutes to develop an effective diffusion case. A plasma spray can also be used to apply the aluminum.

After the diffusion has proceeded to the desired extent, the foil can go directly through a cool-down and then through a leaching solution. A very desirable leaching for 1010 steel is with a 10% aqueous solution of NaOH or KOH held at 170° F. to 212° F. Only about three minutes are generally needed. Keeping the leaching solutions below 140° F. may call for the leaching to take as long as thirty minutes or a little longer. Leaching solutions having 15 or more percent caustic act more rapidly. About 1 to 2 grams of tin as sodium stannite is preferably present per liter of leaching solution.

The leached foil is now in activated condition and can be wound onto the take-up reel with or without a rinsing off of any of the leaching solution dragged out by the moving foil. Rinsing is preferred, particularly where the leached foil is to be stored for more than a few hours. Prolonged contact with residual leaching solution diminishes the activity of the leached product and also tends to decrease the adhesion of the activated surface to the core of that product. The activity of the activated surface is preferably preserved by confining the leached product in an inert atmosphere such as nitrogen or argon, or by covering it with a protective liquid like glycerine. Volatile liquids like acetone and nonane will also protect the activity, but need to be in closed containers to prevent their escape.

All of the foregoing manufacturing steps can be conducted in an enclosed, generally gas-tight chamber as described and illustrated in Ser. No. 281,405, and as there shown the preliminary cleaning step and the leaching and take-up reeling can, if desired, be outside the chamber.

The leaching generates substantial quantities of hydrogen that can be used to flush out the atmosphere in the chamber and thus help protect the heated foil from attack by water vapor or steam generated from the leaching solution and from an electrolytic or non-electrolytic cleaner. A complete coating of liquid aluminum also protects the incoming steel and iron foils even at 1650° F. However, a hydrogen-rich atmosphere presents the danger of explosion, and it is accordingly desirable to inject into the treatment chamber a stream of inert gas such as argon or nitrogen at a rate that keeps the chamber atmosphere below its explosive limit.

By way of example, a one-meter-long induction coil furnace can be provided for coated foil to move through at the rate of two meters per hour, followed by a five-centimeter gap through which the foil cools by radiating its heat to the surroundings, and then a ten-centimeter travel through a leaching bath held at 190° F. Following that bath the foil moves through a falling stream of rinse water that terminates the leaching, rinses off the leachant, and cools the foil to about room temperature. The water-wet foil can then be dried under argon and spooled.

There is generally no need to use a diffusion coating energizer such as ammonium chloride in the atmosphere adjacent the surface being diffusion coated by the foregoing technique, but it can be used and will then help if the incoming coil has not been completely cleaned. Blasting with a stream of blasting grit generally does an adequate cleaning. With or without an energizer in an inert or reducing diffusion atmosphere, a continuous spray of aluminum on a continuously fed foil, or a continuous passage of such a foil through or on a body of molten aluminum, does not leave the objectionable roughness described above for the dipping of individual workpieces in molten aluminum.

However, the smoothness of the sprayed-on aluminum layer does not assure suitable diffusion aluminizing when the diffusion step is conducted at elevated temperatures, i.e., above 1300° F. Thus, a two-mil thick 1010 type steel when sprayed with molten aluminum and rapidly heated to 1450° F. where it is kept for 30 minutes and then cooled, becomes wrinkled and distorted. A similar distortion problem is experienced by a 10-minute diffusion heat at 1600° F. Such wrinkling and/or distortion makes it awkward to manipulate the foils, but essentially entirely disappears during the leaching, and so does not significantly prevent the tight packing of such activated foils in containers for use as thermal decoys as described, for example, in Ser. No. 281,405. Sprayed-on aluminum coatings weighing from about 5 to about 30 milligrams per square centimeter, whether sprayed on as molten aluminum or as a slurry of aluminum particles, lead to the wrinkling and distortion.

For activating only one face of the foil, the other face can be protected or masked against diffusion, or the aluminum spray coating can be confined to the one face to be diffusion coated. This also leads to distortion and wrinkling.

Pre-alloying the aluminum with 5% to 15% silicon by weight reduces the wrinkling and distortion, but does not eliminate them completely. However, the diffusing in of a pre-coated foil yields after leaching an activated product having a thermal output when exposed to air, somewhat less than that of foils prepared by pack diffusion. Alloying with other materials such as zinc, calcium, germanium, magnesium, nickel and boron, also reduces the wrinkling and distortion but has less of an adverse effect on the thermal output. Conducting the leaching at elevated temperatures such as over 220° F., and particularly with aqueous solutions of at least 20% caustic soda or potash by weight also helps.

Wrinkling and distortion can also be reduced by conducting the diffusion at lower temperatures. Below about 1000° F., the wrinkling and distortion is completely prevented, but the diffusion time is increased to as much as four hours or more. Also at these low temperatures ammonium chloride is not a preferred energizer and pack diffusion is simpler to conduct. Such low-temperature pack diffusion is best conducted with extra precautions to avoid side reactions such as etching, that are caused by the presence of moisture. Thus anhydrous water-insoluble $CrCl_3$ can be used as the enerqizer or the diffusion-coating pack can have embedded in it one or more packets of anhydrous aluminum chloride in which that energizer is sealed in an envelope made of plastic sheeting that melts and decomposes at about 300° F. to 600° F. Polyethylene and polyethylene terephthalate plastics are suitable for this purpose. As the packet-containing diffusion-coating pack is heated to diffusion-coating temperature in a loosely covered retort contained in an outer retort whose interior is kept flushed with argon or the like, any moisture in the inner retort is first driven out and flushed away, after which the packet walls melt and decompose to liberate the anhydrous aluminum chloride so that it can volatilize and effect the necessary energizing. If it is desired to minimize the presence of carbonaceous material such as that resulting from the plastic melting and decomposition, the packets can be made of aluminum foil folded over and cemented together by means of a very thin plastic coating.

Wrinkled and distorted foils can also be subjected to a flattening treatment as by rolling between thickness-reducing rollers. The pressure applied by these rollers should only be enough to effect very little or no thickness reduction.

The leaching of aluminum from aluminized cases to provide an activated substrate has been described in the art as conducted in various manners. Reference is hereby made to U.S. Pat. Nos. 3,637,437 (col. 5), 3,809,658 (cols. 1 and 2), 3,939,097 (cols. 4, 6 and 7), 4,206,081 (col. 2), 3,809,658 (cols. 1 and 2), 4,292,208 (col. 9 and the listed references), 4,179,412 (cols. 3 and 4), 3,637,437 (col. 5), 4,040,981 (cols. 2 and 4), and Japanese published Application No. 55780/1976.

In some cases, it is desirable to conduct the leaching at relatively low temperatures, at 140° F. or 160° F., for example. Thus, a cold leaching bath of 10% to 20% by weight NaOH in water with or without a cold water jacket and/or agitation during leaching of aluminized iron foils originally 1 mil thick, can have its temperature rise limited so that it gets no hotter. About 20 to 40 minutes of such low-temperature leaching yields highly pyrophoric iron foils. Even lower leaching temperatures can be used.

For the most vigorous pyrophoricity, an aluminized case depth about 2 mils thick should be provided on an object in which such case represents about 80% of the total thickness of the aluminized object. As noted above, the forming of an aluminized case increases the overall thickness of the original object by about three-fourths the case depth. For the above-noted thick case, leaching with the 50% solution at boiling for one minute develops a pyrophoricity that causes the substrate to heat up to over 1000° F. when it is subsequently dried and exposed to the air. To get hot enough on a stainless steel to scorch paper, it is preferred to provide a case depth at least one-sixth the total thickness of the body of a stainless steel article, where the activated case is only on one face, or at least one-twelfth that thickness where both faces are activated.

Pyrophoric stainless steel screens and foils can be prepared on a continuous basis, as described above for the plain steel foils. Such continuous treatment can be used to prepare pyrophoric or non-pyrophoric products depending upon whether the foregoing control limitations are observed. Thus, very high pyrophoricity is developed with type 430 stainless steel screening woven from 20 mil thick wire aluminized with a 2-mil-thick case having a surface aluminum content of 50 weight percent, leached for only about ½ minute with a 50% aqueous solution of NaOH held at about 280° F. Leaching solutions as strong as saturated aqueous caustic can be used at temperatures as high as 300° F., even shorter leach times being then preferred, but 40% NaOH solutions at 160° F. are preferably used for as long as 30 minutes to develop high pyrophoricity. It is not helpful to have stannite tin present in leaching solutions that are used to leach stainless steels.

Where the leaching solution is stronger than 50%, as for example when using solutions that are saturated with caustic at the leaching temperatures, the leaching times are further shortened by about 1% for every degree Fahrenheit increase in leaching temperature above 290° F. A leaching solution that has been used loses a little of its activity both because some or its caustic is consumed and because soluble aluminate salts are formed in it. A leaching bath originally having a 50% caustic concentration but used to the point that its caustic concentration has been reduced to 40% by weight, actually has a leaching action more closely corresponding to a fresh 35% caustic concentration.

EXAMPLE 3

A type 430 stainless steel 50×50 wires per inch screen woven from 10 mil thick wires is aluminized in a simple pack of 20% aluminum powder and 80% powdered alumina, with 0.5 $AlCl_3$ added as energizer. A 20-hour hold at 850° F. under hydrogen, yields a 2-mil thick case that is then leached with 30% aqueous NaOH for 2½ hours at 110° F. to give a product that will scorch paper after rinsing, drying and then exposed to air. After it has completed its pyrophoric reaction with air it makes a very effective catalyst for reducing NOX in internal combustion engine exhausts and coal-burning furnace smokestacks by reaction with a little $NH_3$ at about 300° C. to 375° C. It also makes a good catalyst for oxidizing ammonia to nitric oxide, for decomposing ammonia into nitrogen and hydrogen, and for synthesizing ammonia from nitrogen and hydrogen.

EXAMPLE 4

A 60×60 wires per inch screen of type 304 stainless steel woven from wires 8 mils thick, is aluminized as in Example 2, but with $NH_4Cl$ substituted for the $AlCl_3$, an aluminizing temperature of 1650° F., and the time at that temperature two hours. After cool-down the screen is removed from the coating pack and dropped into 25% aqueous caustic by weight held at boiling for 30 to 60 seconds, then immediately rinsed. Upon drying it shows a pyrophoricity even greater than the screens of Example 3.

Using a fine-wire thermocouple, pyrophoric temperature increases to over 900° F. have been measured with type 430 stainless steel screens aluminized as in Example 3 and leached as in Example 4.

The foregoing pyrophoric activity is imparted by the same process to other iron-chromium and iron-chromium-nickel alloys containing over 5% and as much as 30% chromium. The crystallographic structure of these alloys can he of any type, including austenitic, martensitic and ferritic. Specific stainless steel alloys suitable for such treatment include 25-12 stainless steels, as well as types 316, 321 and 347 and iron containing 12% chromium and the types 304 and 430 stainless steel already noted. Although some of these stainless steels are not true steels inasmuch as they contain little or no carbon, they all come within the stainless steel category of the present invention.

As pointed out above, the diffusion aluminizing conducted to provide pyrophoric stainless steels is very effective when carried out at temperatures of about 800° F. to about 1650° F., and is followed by a vigorous leaching with aqueous caustic having at least 25% NaOH by weight. If more than about 15 milligrams of aluminum is leached out per square inch by vigorous leaching with aqueous caustic having at least 45% caustic, the leached case become loosened and can then be removed by rubbing, for instance.

The pyrophoric stainless steels are strongly catalytic as well as pyrophoric, and remain strongly catalytic when the pyrophoricity is lost as by reacting with air or by dipping in 3 volume % $H_2O_2$ in water. Thus, the pyrophoric stainless steels are particularly effective catalysts for reducing NOX emissions from furnace stacks and the like with the help of $NH_3$ or reducing gases, as described in Ser. Nos. 479,211 and 302,979. For such use these pyrophoric catalysts can be merely permitted to react with air before, during or after they are installed in the stack. However, they can alternatively have their pyrophoricity eliminated by $H_2O_2$ treatment, if desired.

The pyrophoric stainless steels, like non-pyrophoric stainless steels, show their maximum catalytic effectiveness for NOX reduction at temperatures below about 350° C. They are accordingly very desirable for such use, as for example, in the arrangements described in Ser. No. 479,211 and illustrated in its FIGS. 2 and 3, and those aspects of that parent application are hereby incorporated herein as though fully set forth.

The pyrophoric stainless steel is also very effective for catalyzing the formation of ammonia as well as its decomposition, and the oxidation of ammonia to nitric oxide. For such purposes the catalysts are preferably in the form of wire screening as described in Ser. Nos. 302,979 and 479,211, or in the form of tubing as described in Japanese Patent Application No. 55780/1976, or can be fabricated or even cast in any other desired shape.

The maximum temperature attained by a pyrophoric metal foil or screen when it undergoes its pyrophoric action, also depends on the proportion of activated surface to non-activated core. Inasmuch as the catalytic action of the activated surface is essentially unaffected by how much unactivated core is under it, an activated catalyst can have a very thick core and thus appear not extremely pyrophoric as indicated by its temperature rise upon exposure to air, yet be a highly effective catalyst. However, for catalytic purposes it is preferred, particularly for gaseous reactions, to have the catalyst surface undiluted as much as practical by inactive core. This preference, considered with the greater effectiveness of the surfaces that have been more intensively pyrophorically activated, accordingly makes it desirable to have the pyrophoricity as vigorous as practical, even when the pyrophoricity is removed by an after treatment after it is developed and before catalytic operation is started.

For NOX reduction the stainless steels can, before activation, contain helpful alloying metals such as vanadium, manganese, and other metals referred to in Ser. Nos. 302,979 and 479,211. Thus, type 316 contains molybdenum, type 321 contains titanium, and type 347 contains columbium. These alloying metals can be present in the original stainless steel, or they can be placed or diffused into the surface to be activated, or they can be alloyed with the aluminum that is to be diffused in as the first step in the activation. The content of any of these alloying metals is preferably at least about 5% weight of the activated case.

The presence of about 10% manganese in the surface of those stainless steel catalysts improves their effectiveness, particularly in stack gases containing high sulfur dioxide content, but the improvement is gradually lost over a span of about a day or so. A typical diffusion coating with manganese is conducted at 1725° F. for five hours with a diffusion coating pack of:

| | |
|---|---|
| 53 g. | manganese powder |
| 212 g. | $Al_2O_3$ powder |
| 3 g. | $NH_4Cl$ powder |

It can also be used to diffuse manganese into nickel as well as nickel alloys other than stainless steels. On nickel it gives a weight gain of about 21.9 milligrams per square centimeter, and a case depth of about 1.4 mils.

The manganese-carrying nickel and other nickel alloys have improved catalytic action, for example, in the oxidation of formaldehyde to formic acid, as well as in the methanation of CO. Nickel-cobalt-molybdenum alloys heretofore used in such methanation are particularly improved.

A manganese content over about 20 weight percent in the outer skin of any of the foregoing catalysts does not seem to be worth the trouble.

For NOX reduction of internal combustion engine exhausts, the foregoing catalysts, or any similarly reacting catalyst is placed in the exhaust line, preferably close to the exhaust ports of each engine cylinder or combustion discharge. Where the exhaust line includes a converter that oxidizes carbonaceous gases, the catalyst can be fitted to the converter outlet.

A small stream of ammonia is introduced into the exhaust so that it can react with the NOX in the exhaust. Where there is an engine-driven pump that injects air into the exhaust, the intake of that pump can be connected to a source of ammonia such as a container of ammonia-evolving material like ammonium carbamate or ammonium carbonate or ammonium bicarbonate. Liquefied ammonia can also be used, but must be kept under high pressure. The container is kept closed when the engine in not operating, but when operating its contents deliver a gradual stream of ammonia or ammonia-containing gases which are pumped into the hot exhaust with or without the air the pump delivers. A pump with an operating speed controlled by the engine speed does a very good job of metering the desired ammonia content into the hot exhaust. The metering rate is easily adjusted so that the exhaust as discharged into the atmosphere has no ammonia odor.

With either arrangement, the ammonia-supplying container is conveniently vented to a supply of absorbent such as a carbon-filled canister which can be the same or different from the canister generally used to absorb gasoline vapors. The vent can be controlled by a valve which is normally closed but opens to relieve excess pressure as well as in response to intake suction.

The use of an ammonia feed reduces the need for exhaust gas recirculation, which can then be diminished or entirely eliminated. More power is then obtainable from the engine.

For ammonia oxidation to nitrogen oxides, the pyrophoric or non pyrophoric stainless steel screens activated by aluminizing and leaching can merely be substituted for the platinum screens used in the prior art reactors with a reduction in operating temperature to 700° C. or below. The pyrophorically activated screens are preferred, particularly when their porous catalytic surface is partially impregnated with potassium salts such as potassium carbonate or vanadate.

Diffusion coating packs in which the pack particles are very small, are particularly suited for diffusion coating the interiors of hollow articles. Some types of such interior coating are described in U.S. Pat. No. 3,936,539, and others in parent Ser. No. 230,333.

A modified form of aluminum diffusion and leaching can also be used for applying coatings. In this modification there is first prepared an alloy of aluminum containing relatively small amounts of other metals to be coated onto a substrate. This pre-prepared alloy contains sufficient aluminum to bring its melting point down to 1800° F. or below, preferably 1400° F. or below. It can then be readily flame-sprayed on a workpiece, or the workpiece can be dip-coated in the molten alloy, and if desired the resulting coated workpiece heated in a protective atmosphere to improve the bonding. Where a protective atmosphere is used, it can be that of a diffusion coating activator like $NH_4Cl$ or $NH_4F$ or $NF_4HF_2$.

After the coating is completed, the coated workpiece is then dropped into a leaching bath that dissolves out most of the aluminum from the coating. Where some specific amount of aluminum is desired to be present in the coating after the leaching is completed, the leaching is terminated before the residual aluminum content drops too low.

After the completion of the leaching the workpiece has the desired coating, but the coating is in a microporous condition due to the voids introduced where the aluminum has been leached out. In such condition the coating is particularly receptive to receiving and anchoring top layers such as ceramic thermal barrier applied over jet engine vanes and blades.

A particularly desirable coating is the MCrAlY and MCrAlZr type coatings described in U.S. Pat. No. 4,005,989 and in the U.S. Department of Energy report DOE/NASA/259-26 NASA TM-81685 dated February 1981. Although these coatings contain only about 12 to about 15% aluminum by weight, a good aluminum-rich starting alloy for dip-coating or flame-spraying contains about 40 to 50% aluminum with the remaining alloying ingredients in the desired final proportions. About 3 hours of leaching in 20% aqueous NaOH at 140° F. subsequently removes essentially all the excess aluminum. The MCrAlY type coatings should not be leached too vigorously because the yttrium tends to be leached out by strong hot caustic.

After the leaching the leached products are rinsed and then top-coated with a mixture of extremely fine particles of $ZrO_2$ and $Y_2O_3$ as described in the above-cited Department of Energy report and the references cited therein. Such top-coatings generally have the $ZrO_2$ and $Y_2O_3$ in a molar ratio of from about 1:8 to about 1:12. Such mixtures can be slurried in water and the leached workpiece dipped in the slurry. The workpiece is now fired at about 2000° F. for a few minutes to secure the oxides in place, and the dipping and firing repeated to form an effective thermal barrier that can be about 5 to about 15 mils thick.

The "M" of the MCrAlY and MCrAlZr can be nickel, cobalt iron or mixtures of any two or all three of these metals.

By activating only one face of a foil, as described for example in Ser. No. 172,671, the activation can be made to penetrate most of the way through the foil thickness, leaving only about 20% of that thickness as a structural backbone. The unactivated face of a stainless steel or plain iron foil can be plated with aluminum to improve its radar reflection characteristics. The so-called Schoop aluminizing with a spray of molten aluminum is effective to deposit an aluminum film only about 0.1 to 0.3 mils thick on the back of a roll of activated foil as it is unspooled and then respooled in an Argon box. A layer of copper or even silver can be similarly deposited in place of the layer of aluminum. Copper and silver are not attacked by leaching baths, so that they can be deposited before or after the leaching.

The radar reflectivity associated with pyrophoric foils is also increased by mixing them with standard aluminum radar chaff or foils. Such aluminum chaff or foils only about ½ mil thick or thinner, mixed with two to five times as many pyrophoric one-inch discs of iron foil, make an effective heat and radar decoy when ejected as a mass from an exploding cartridge.

The cleaning of substrates before they are diffusion coated calls for a high degree of care and attention. This is generally not too much of a problem when the substrates are newly manufactured articles which have been protected against oxidation and soiling. A thorough blasting with grit or glass particles, with a solvent degreasing or electrolytic cleaning is generally quite adequate.

However, substrates which have been subjected to oxidizing action, particularly at high temperatures, generally need an even more vigorous treatment. Thus, jet engine hot section airfoil blades are normally aluminized by a diffusion coating before use, in order to properly withstand he high temperature exposure to fuel combustion gases and the like. A newly manufactured blade that has not been used cleans up very easily with the blasting and degreasing, but after use for a substantial period of time will require re-aluminizing. For this purpose it has been found desirable to subject the used blade to a stripping treatment as described in U.S. Pat. No. 4,327,134, in order to remove what is left of the previously aluminized surface of the blade. The stripped blade was then subjected to a fluoride bright annealing treatment so as to reduce all effects of long high-temperature oxidizing exposure, and be ready for re-aluminizing. The bright annealing removes oxides from crevices and cracks in the blade, and leaves the blade in condition to receive any desired further treatment. Thus any repairs to the blade, as by welding cracks and building up eroded areas, can be easily effected after such bright annealing.

According to the present invention a modified bright annealing is applied directly to the used blade before stripping, and the bright annealing arranged to also remove the residual aluminum from the previously aluminized layer.

Figure 1:
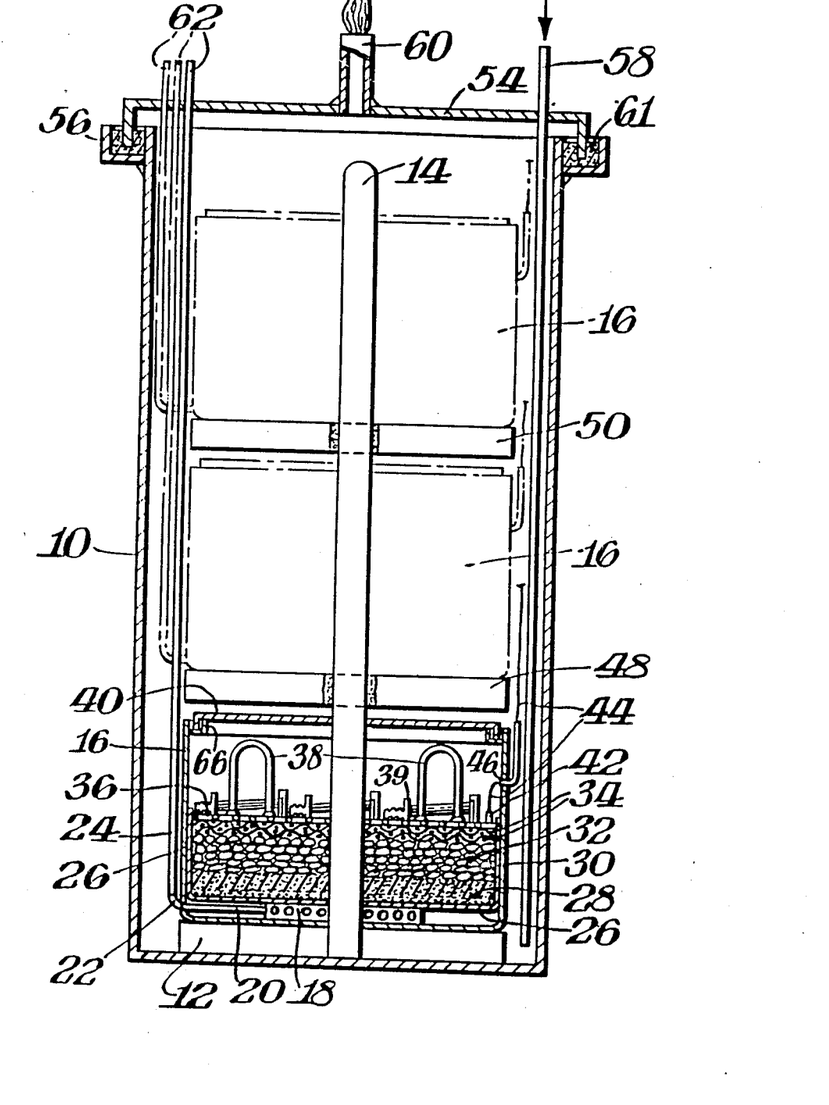

The modified bright annealing is illustrated in the drawing figure as conducted in an Inconel 600 retort. A rack 12 having lifting arms 14 is lowered into retort 10 and has a bottom ring 14 that supports an inner retort 16. On the floor of the inner retort is a sparger box 18 connected by tube 20 to an outer connection 22 for a gas supply conduit 24. On box 18 is placed a basket 26 that holds the reactants. The floor of the basket is barely covered with a layer 28 of about 325 mesh chromium powder about millimeter deep. Over this layer is poured in a two-millimeter deep layer 30 of the following mixture:

| powdered $NH_4HF_2$ | 86% by weight |
|---|---|
| powdered $CrF_2$ | 12% by weight |
| powdered chromium | 2% by weight |

On top of layer 30 there is applied a ½-centimeter deep layer 32 of chromium granules about 5 to about 20 millimeters in size, and this is then covered with two 60 by 60 mesh screens 34 made of nickel wire 4 to 20 mils thick over which a nickel rod grid 36 is placed. The grid has handles 38 for convenient handling. Nickel-base superalloy blades that have been used in an engine and need overhaul, as at 39, are then placed directly on the grid 36 and can be piled in over them to depths of up to about six inches. If desired, an additional nickel screen can be placed over the floor of the grid. The inner retort as so loaded is loosely covered with a lid 40. One or more thermocouples 42 can be placed among the blades to check the temperatures to which they are subjected, and the thermocouple leads 44 run through a tubular port 46 to outside the inner retort.

Rack 12 has additional rings 48 and 50 to hold additional inner retorts that can be packed like retort 16. Thus loaded, the rack 12 is lowered into the outer retort 10. A cover 54 is then fitted into a trough seal 56 at the top of the outer retort, cover 54 carrying an inlet tube 58 which reaches down into the very bottom of the outer retort, and also carries one or more discharge tubes 60. Additional passageways 62 are provided for the thermocouple leads and spargers for each inner retort. Finely divided alumina powder 61 poured into trough seal 56 to block access through that seal. There is no reason to block access to the inner retorts, so that where they also have trough seals as at 66, the troughs of those seals are preferably kept empty. Aside from the nickel screens and grid, all parts are preferably made of Inconel-600 or Inconel-800.

The bright anneal treatment is carried out on used blades which have been subjected to a cleaning as by wire-brushing and grit blasting. After the retorts are loaded as set out above, a shell furnace is placed around the outer retort and started up to apply heat, and a stream of argon is fed in through tubes 58 and 62. After the thermocouples reach about 300° F. and the argon has flushed out the air from the retort assembly, a stream of hydrogen is substituted for the argon, and the hydrogen flow held down to about 1 cubic foot per hour in each inner retort, and about 12 cubic feet per hour through the outer retort. A flame can be applied to the vent 60 to burn off escaping hydrogen.

The thermocouples will reach 1700° F. after several hours, and the furnace heating then controlled to keep the thermocouples between about 1700° F. and 1750° F. for twelve hours. The heating is then stopped and the retorts permitted to cool. The furnace can be removed from around them to speed the cooling.

When the thermocouples fall to about 300° F., the hydrogen stream is replaced by an argon stream to flush out the hydrogen before the retorts are opened and the blades removed. They are now very shiny in appearance and show very little surface aluminum, even when the blades are air-cooled hollow blades that had previously been aluminized inside and outside. Indeed, the originally diffused-in aluminum is essentially all gone but the blade's dimensions are substantially unchanged so that hollow blades with very small wall thicknesses can be reused more often. Stripping of the prior aluminized case by the process of U.S. Pat. No. 4,327,134 generally leaves the blade with about $\frac{1}{2}$ to $\frac{3}{4}$ mil of its surface removed, as compared to the original blade before the original aluminizing. Hollow blades aluminized inside and out and then stripped inside and out, suffer such surface removal both inside and out.

It should also be noted that the nickel-base superalloys such as B-1900, IN-713, IN-600, IN-738 and Hastelloy X, from which such vanes are made are not deleteriously affected by the hot fluoridizing treatment if the maximum temperature is not higher than about 1750° F. At higher temperatures some intergranular attack tends to occur. At temperatures below 1700° F., the time of treatment is lengthened, and below about 1650° F. the time required is too long to be practical.

After the fluoridizing treatment of the present invention, the blades are ready for re-aluminizing, preferably by pack diffusion in a powder pack of a mixture of:

| | |
|---|---|
| powdered aluminum-silicon alloy (88:12 aluminum to silicon by weight) | 20% by weight |
| powdered alumina | 80% by weight | with $\frac{1}{2}$% powdered NH$_4$Cl added by weight of that mixture. A six-hour treatment at about 1400° F. is very effective, followed by post diffusion at 1975° F. for 4$\frac{1}{2}$ hours in hydrogen, and then aging at 1650° F. for 10 hours in hydrogen or argon.

Aluminizing as in U.S. Pat. No. 3,801,357 is also suitable.

Where the fluoridized blade has narrow cooling passageways, the re-aluminizing is best carried out by the process described in U.S. Pat. No. 4,347,267. Different parts of the blade can be aluminized by different techniques so that, for example, the interiors of hollow blades can be aluminized by the slurry technique of U.S. Pat. No. 4,347,267, while their exteriors are aluminized by a gas aluminizing.

Other nickel-base and cobalt-base engine jet parts such as vanes and combustion chambers, are also well suited for the foregoing re-conditioning treatment.

The fluoridizing action is essentially an exposure to an atmosphere containing a low concentration of hydrogen fluoride, and any other means for supplying hydrogen fluoride at a concentration of about $\frac{1}{8}$% to about $\frac{1}{2}$% by volume in hydrogen, can be used. Where the fluoridizing atmosphere is developed by decomposing NH$_4$HF$_2$ as in the drawing, that atmosphere is best not flushed out too rapidly, as by keeping the hydrogen flow in the inner retorts down to not over about 1% of the space in the inner retort, every minute.

The flow of hydrogen can be completely eliminated as by use of glass-sealed inner retorts such as through the technique described in U.S. Pat. No. 2,844,273. Sand seals can also be used but do not make perfect seals. Care may be needed to keep the glass and sand of those seals from consuming too much HF.

The layers 28 and 32 can be eliminated from the inner retort 14, in which event the layer 30 which is where the hydrogen fluoride is generated, is best reduced in thickness to about 1 millimeter. It is important that the workpieces be spaced from the NH$_4$HF$_2$ and are best separated by at least two nickel screens. The workpieces preferably have their least critical surfaces placed on the nickel screens. Thus, in the case of jet engine hot section blades, the blade roots take little or no aluminizing, and are best located against those screens.

Cobalt base superalloy workpieces such as used jet engine hot section vanes can also be fluoridized and re-aluminized by the foregoing technique, but for these workpieces the fluoridizing temperature can range to as high as 1850° F. inasmuch as they are not particularly susceptible to intergranular attack.

A pyrophoric powder or powder mixture can be used as a thermal decoy against heat-seeking missiles, as by projecting them into the air from a sealed container. They can, for example, be compressed or bonded into discs or rods and projected in that form. Such decoy materials can also be given radar chaff characteristics, as by inserting them into thin-walled aluminum or copper tubes about an inch long or longer—for example, 6 to 8 inches. A quantity of such powder having particles about 20 microns or less in size can be extruded with the help of a polyethylene or polystyrene binder into elongated rods about 7 to 15 mils thick, and the rods wrapped in a turn of aluminum foil $\frac{1}{2}$ to 2 mils thick. The wrap can be held in place by the binder, using heat or solvent to cause it to adhere to the extruded rod or to a small overlap of the wrap. Cutting such a wrapped assembly into suitable lengths, preferably leaving the cut ends open so that air can get to the powder within the wrap, can complete the production, but care should be taken to conduct all of the steps while the powder is protected as by a film of water, from contact with oxygen.

Instead of or in addition to the open ends of the cut lengths, the wrap itself can be perforated to permit more ready access of air to the wrapped powder. On the other hand, such access can be hindered by increasing the proportion of binder to powder, and/or impregnating the powder particles with colloidal inert particles as described in Ser. No. 281,405 or with slowly volatilized liquids as described in Ser. No. 571,510.

According to the present invention pyrophoric Raney iron particles, whether or not they contain diffused-in boron, can be safely stored in air, if they are first brought into good thermal contact with a heat sink at about 35° C. or less and while in such thermal contact exposing them to air or oxygen in such a way that the particles do not increase in temperature by more than about 5° C.

Where the particles are not over about 2 millimeters in size, they can be spread on a single-particle layer on a metal plate, preferably aluminum or copper, at least about 2 millimeters thick, as by pouring into such plate a slurry of the actively pyrophoric particles in water and then permitting the water to evaporate. A stream of air directed at the layer, as by a fan, greatly speeds the evaporation. The resulting particle layer can then remain on the plate exposed to air at 35° C. or less for a few minutes to assure that the water is completely evaporated off and the particles have all been stabilized.

Pyrophoric particles of any size can be similarly stabilized by contacting them with aqueous potassium nitrate for from 1 to 24 hours. At least about 5 grams per liter of such nitrate solution will provide the stabilization after about 20 hours of contact at room temperature. Other nitrates behave similarly, as do nitrites.

Pyrophoric iron and nickel foils can also be stabilized, preferably by suspending them in cold water and bubbling air through the suspension. Such pyrophoric foils can be made on a large scale basis by starting with a commercial aluminum-dipped 3 to 6 mil iron foil containing about 3 mils aluminum on each face, cold reducing the dipped product to about one-third its thickness, and then heating the cold-reduced material at about 600° C. in an aluminum chloride atmosphere for about three hours to yield a product about 1½ to 3 mils thick both surfaces of which are very rich in both aluminum and iron. This product is then leached as indicated above. The aluminum into which the iron foil is dipped can contain up to about 12% silicon, and a dip coating of such aluminum-silicon alloy is less likely to delaminate.

Iron or nickel foil can also be activated by unreeling from a spool and passing it through an aluminizing retort, preferably while holding a wide strip of the foil on its edge so that it is in a vertical plane. The aluminizing is uniform particularly where the aluminizing is effected with a diffusion powder pack as described in Ser. No. 172,671. The aluminized foil can then be passed through a leaching tank.

Regardless of how an activated leached iron or nickel surface is obtained, it can used for many catalytic purposes including the oxidation of methane, and such use is improved by depositing on the surface a film of platinum or palladium, or a thin layer of fine zirconium oxide powder. Metal films are readily deposited by electroplating or in the case of platinum-family metals by decomposing the chloride or other salt of such metal. Powders can be applied by mixing them with colloidal alumina or silica in suspension in water, then applying the suspension and finally permitting the water to evaporate. The $ZrO_2$ changes the wave length of the radiation emitted when the activated surface pyrophorically reacts.

Stabilized by any of the foregoing techniques, the particles will not show pyrophoricity if kept in air at about 50° C. or less. However, when heated to about 100° C. or higher, they promptly begin reacting with air and go through a pyrophoric stage to completion. The heat thus generated and the maximum temperature reached in such stage are slightly less than those obtained from unstabilized particles, but more than adequate for most pyrophoric uses. Some of the stabilized products will pyrophorically ignite when heated to temperatures of 90° C. or somewhat below.

To achieve the above-described stabilization the leached iron-boron-aluminum alloy should have at least about 25% boron. An alloy stabilized to 50° C. will show stability to about 70° C. when mixed with the $Ba(NO_3)_2$.

A stabilized pyrophoric iron-aluminum-boron corresponding to $2FeB_2.3AlB_2$ is magnetic and will remain stable even at 90° C. Such a pyrophoric alloy can be made by leaching with caustic soda an alloy of:

| |
|---|
| 33.9 wt % Fe |
| 33.3 wt % B |
| 32.8 wt % Al |
| (FeB.2AlB$_2$) | which alloy is not magnetic. Even without leaching, such high-boron alloy decomposes $Ba(NO_3)_2$ very effectively when both are 40 micron particles well mixed and heated to ignition. A hot soldering iron will ignite the mixture or will more rapidly ignite a small amount of igniter mixture of 2 parts by weight stabilized pyrophoric iron powder, and 1 part by weight sodium chlorate powder placed over the $NO_2$-generating composition.

Such a reactive unleached iron-aluminum-boron alloy should have about 25% to 40% boron by weight and about 28% to about 50% aluminum by weight.

Stabilized pyrophoric iron particles containing 6% to 30% diffused-in boron by weight, can be mixed with five to seven times their weight of powdered anhydrous $Ba(NO_3)_2$ to form a composition that is stable at room temperature, but upon heating reacts to evolve copious quantities $NO_2$. With less diffused-in boron, the reaction is more difficult to initiate and maintain, but the addition to such a less reactive composition of about 3% to about 10% powdered elemental boron and/or oxidizer such as sodium chlorate, makes its action positive and complete.

All the particles are preferably not over one millimeter in size. The stabilized pyrophoric particles can be as low as one-eighth the weight of the barium nitrate, and preferably no greater than about one-third that weight.

Powdered boron alone will react with $Ba(NO_3)_2$, when heated, and thus liberate $NO_2$, even when mixed in a proportion by weight of one part boron to 16 parts $Ba(NO_3)_2$. Such a mixture has low thermal conductivity, a characteristic that is improved by the use of pyrophoric metals. Non-pyrophoric metals such as zirconium or coorse iron or nickel powder can also be used.

Substituting anhydrous $Sr(NO_3)_2$ for the barium nitrate in the foregoing compositions gives similar but less vigorous results, even when the oxidizer content is raised to 15%. Anhydrous calcium nitrate produces still less vigorous compositions. Hydrated forms of the foregoing nitrates are somewhat less vigorous in their decomposition, as compared with anhydrous forms. Other nitrates such as ferric nitrate, ferrous nitrate, nickel nitrate, aluminum nitrate, copper nitrate, chromium nitrate, as well as the corresponding nitrites, are similarly decomposed, some with even more vigor than others, whether or not hydrated. Indeed, ferric nitrate in hydrated form can be very effectively decomposed by pyrophoric iron-boron alloy containing as little as 5% boron.

Up to about 15% of iron dust can be added to the foregoing compositions without detracting significantly from their effectiveness or the vigor of the reaction with $Ba(NO_3)_2$, but this reduces the volume of $NO_2$ generated. Such dust should have particles about 10 microns or less in size.

The foregoing $NO_2$-generating pyrophoric particles can be used without being stabilized, but then the compositions are required to be protected against contact with oxygen until the $NO_2$-generation is desired. Such protection can be provided by keeping the reactive compositions in a sealed argon-or nitrogen-filled frangible container that is broken when the $NO_2$ generation is to start. No pre-heating is needed. Such a frangible container can be made of glass or very brittle metal such as iron aluminide, and the breaking of the container can be assisted by a percussion cap or the like.

Pyrophoric nickel powder can be used in the foregoing composition in place of pyrophoric iron powder.

Magnesium powder should not be added to any of the foregoing powdered compositions inasmuch as such addition tends to render the compositions explosive. Thus a mixture by weight of four parts magnesium powder, two parts boron powder and 32 parts anhydrous barium nitrate powder, all particles being smaller than 100 microns, will upon heating violently detonate even if in an open container. Molar proportions of boron:magnesium:nitrate radical of 1:1.2:1.5 plus or minus 25% for each ingredient, are dangerous in this respect.

Boron powder alone will decompose $Ba(NO_3)_2$, and will decompose as much as 16 times its weight of such nitrate, but is difficult to ignite. Adding 5% by weight of pyrophoric Fe-B-Al alloy or even the above-noted active non-pyrophoric Fe-B-Al alloy simplifies the ignition.

Pyrophoric Fe-B-Al alloys containing less than about 4% B will not do a good job of decomposing $Ba(NO_3)_2$ unless at least about 1% elemental B powder is added to the $NO_2$-generating mixture.

The boronized Raney iron particles of the present invention are also effective to decompose polytetrafluoroethylene resin and in the presence of a source of oxygen generate dangerous fluorine-containing gases. Thus, a mixture of powdered polytetrafluoroethylene with about one-eighth its weight of powdered sodium chlorate, and with about one-fourth its weight of powdered Raney iron in which the iron had been diffusion-alloyed with 6% boron, will react and generate large quantities of fluorine-containing gases. Similar results are obtained whether the Raney iron is stabilized or unstabilized, and even if it contains no boron except that when stabilized it will not begin the gas-generating reaction until it is heated to about 110° C.

A composition very effective for decomposing nitrates as well as polytetrafluoroethylene resin is an aluminum-iron-boron alloy containing by weight about 16.9% aluminum and about 13.5% boron. It is essentially $AlFe_2B_2$.

The gas generation is made more vigorous by increasing the boron content of the Raney iron to about 20% or even higher, or by adding up to about 10% elemental finely divided boron to the resin-containing mixture. Mixtures containing more than about 5% free boron or more than about 10% alloyed boron need little or no air or other oxidizer to effect the gas generation.

Other oxidizers such as nitrates, nitrites, $KMnO_4$, sodium perchlorate, manganese dioxide, sodium peroxide, sodium periodate, sodium iodate, sodium bismuthate and $CrO_3$ can be used. Where the resin is in the form of an open-celled foam weighing about 0.15 gram or less per cubic centimeter, no oxidizer is needed inasmuch as sufficient air will be present in the foam cells. The use of shredded foam in such compositions while keeping the compositions open to the air, permits the use of foams having densities as large as 0.2 gram per cubic centimeter, without extra oxidizer.

The boron-containing Raney iron can also be made without a diffusion treatment. For example, a batch of aluminum is melted, and then iron and boron are dissolved in the melt to make $FeAl_2$ containing about 20% boron by weight of the iron. The melt is then solidified, crushed to a powder, and leached to extract most of the aluminum from the powder. The leached product will still contain as much as 25% aluminum by weight, and is highly pyrophoric.

Nickel can be substituted for the iron in the making of a powdered Raney alloy for use in the foregoing oxidative decomposition of polytetrafluoroethylene resin. Such Raney nickel can also contain boron to increase its pyrophoric heat liberation.

According to another aspect of the present invention, there are provided highly active heat-generating compositions which burn in air when heated, but are essentially inert at temperatures below about 50° C. to 100° C. so they can be convenient stored for use when desired.

As shown, pyrophoric materials prepared by leaching $FeAl_3$ or $NiAl_3$ for example, can be stabilized by subjecting them to a very small quantity of oxygen in a manner that does not permit them to appreciably heat up, the resulting stability tends to break down at about 50° C. or a little higher.

According to the present invention, there a provided pyrotechnic compositions which ignite at temperature above 100° C., e.g., at about 300° C., and have a substantial aluminum content as well as a high thermal output. These compositions are activated aluminides of metals like molybdenum, zirconium and colombium that when not combine with aluminum ignite in air at about 500° C. to 700° C. a atmospheric pressure. These metals are easily combined with aluminum to form alloys or aluminides having two or more atoms of aluminum for each atom of ignitible metal, and when so combined generally have ignition temperatures not much different from that of the pure ignitible metal as noted above. Incorporating about 2% to about 10% boron in such alloy, based on the weight of the ignitible metal, generally lowers the ignition temperature by about 20° C. However, the ignition temperature of the aluminide with or without the boron, is lowered about 100° C. to about 150° C. by activating the aluminide.

The activation of the .present invention is the leaching out of some of the aluminum, as with aqueous caustic soda or caustic potash. For this activation, the aluminum alloy preferably has between about 2.5 and 3.5 atoms of aluminum for every atom of alloyed ignitible metal, and the leaching preferably removes all the aluminum in excess of two atoms per atom of ignitible metal. This is illustrated by the following example:

One kilogram of aluminum covered by a cryolite flux is melted in a stainless steel retort under argon, and there is then stirred into the melt 600 grams of powdered molybdenum. The stirring is continued for about ½ hour while the contents of the retort are maintained at about 1200° C. to about 1400° C. to complete the alloying.

The melt is then permitted to cool and solidify, after which the metal layer is crushed into small pieces and the pieces ground to a maximum particle size of about 0.3 millimeter. The ground product is now poured into an excess of 25% NaOH solution in water. Bubbles are immediately evolved as the caustic attacks the alloy particles, and the evolution begins to noticeably slow down after several hours reaching a very low level after about six hours. The caustic is then poured off, and the residual particles washed wit water and dried.

Thus activated, the particles have a porous surface and are stable in air at temperatures as high as 300° C. However, when a mass of the particles is heated in air to above that temperature, the particles ignite and vigorously react with the air. The reaction is an oxidation and is completed on the smaller particles before it is completed on the larger particles of the ground mass, so that the pyrotechnic effect is more intense for about the first minute, and drops off somewhat for about another minute. On a asbestos pad the oxidizing particles become red hot an gradually crumble to a powder. Such pyrotechnics generate temperatures well over 1000° C., and can accordingly be used to supply heat for the bright annealing or other purposes.

Zirconium and columbium behave very similarly when treated as in the foregoing Example. After activation they ignite at about 350° C. in air at atmospheric pressure, and the ignition point of their aluminum alloy before activation is about 500° C., being not much different from the ignition point of the pure metals.

The activities of the activated alloys are lower when the leaching is terminated earlier, and are also lower when the alloys subjected to the activation have a less than 3:1 proportion of aluminum atoms to ignitible metal atoms. There are also some reactivity increases when the leaching is made more intense, as by starting with a hot or boiling caustic solution, and by increasing the caustic concentration to saturation However, very good reactivity is obtained when the leaching is effected at 20° C., although the leaching is slower at that temperature. At boiling temperatures with saturated caustic, the leaching can be completed in less than two minutes.

It is not essential for the aluminides of the present invention to be prepared by melting. Thus, iron, zirconium, titanium, molybdenum and columbium can be effectively alloyed with aluminum by a thermal diffusion. Fine powders of the separate alloy ingredients can be uniformly mixed in a diffusion coating retort and heated to about 600° C. in an $AlCl_3$ atmosphere for only about six hours to produce usable alloy when the ignitable metal powder particles are no larger than about 10 microns. Larger particles take a little longer. Other halide atmospheres, such as of anhydrous $CrCl_3$, either in its water-soluble or water-insoluble form, or the $AlCl_3$ as the diffusion-energizing atmosphere. Only about ½% to about 1% of such energizer is mixed with the powders to be alloyed.

Tri-aluminides of some of the noted metals are also available as articles of commerce.

The leaching of the present invention can also be effected with inhibited hydrochloric acid such as that referred to supra, but the resulting activation is not as great as produced by caustic leaches.

There can also be included in the foregoing alloys ingredients that improve the pyrotechnic behavior. Thus, about 2% to 20% of boron or magnesium or iron or mixtures of these, are helpful in this respect, and can be added to a melt or to a diffusion-alloying mixture. Also, these metals can be introduced by diffusion into a pre-formed aluminide or by diffusion with the aluminum. For example, 250 grams of powdered $ZrAl_4$ can be mixed with 10 grams of powdered boron and 5 grams of sodium fluoborate, and subjected to a diffusion heat as described in U.S. Pat. No. 3,801,357, but without using inert solid diluent, for three hours at 1800° F. in an argon-bathed atmosphere, to diffuse the zirconium and boron into aluminized nickel powder or $NiAl_3$.

About 1% to about 10% of iron can be similarly introduced into the aluminide with or without the boron, to provide activatable alloys that after activation ignite at temperatures of about 300° C. or a little lower. Magnesium-aluminum alloys can also be activated by the foregoing techniques to provide activated material having ignition temperatures below 300° C. The magnesium-aluminum alloys preferably have, before activation, at least two atoms of aluminum for every atom of magnesium, but can be activated even when the aluminum-magnesium atom proportion is as low as 1½. The aluminum-to-zirconium atom ratio is preferably at least 4:1 but can be as low as 2:1.

Where the aluminized skin of a ferrous metal pipe or other workpiece, has an aluminum content of about 60 atom percent or more, that aluminum content can be decreased by leaching the aluminized surface with hot concentrated aqueous KOH or NaOH. This leaching treatment can be similar to that described in parent application Ser. No. 479,211. Such treatment is more severe than the relatively mild leaching described in U.S. Pat. No. 3,764,371, particularly where the aluminized workpiece is a stainless steel. Type 304 stainless steel aluminized to an aluminum pick-up of 0.5 milligram per square centimeter can thus have its surface aluminum content reduced to simplify welding.

Including 2% to 20% boron in the magnesium-aluminum or zirconium-aluminum alloys, based on the weight of the magnesium or zirconium, also increases their pyrotechnic output.

The foregoing pyrotechnic improvements are also obtained with alloys in the form of foils and sheets, as well as powders.

The boron additions of the present invention can also be effected by the procedures described in U.S. Pat. No. 4,536,215.

The foregoing low-ignition-point activated alloys are readily ignited with an ordinary household match.

A stainless steel workpiece can be provided with a catalytic pyrophoric surface, by first plating the stainless steel surface with nickel or iron, then aluminizing the plated surface, and finally leaching the aluminum out of the plating. Thus, a one to two mil thick acid nickel electroplate on 304 stainless steel can be aluminized at 750° to 800° F. for twelve hours, as in U.S. Pat. No. 4,154,705, to provide an aluminum pick-up of 1.9 to 2 milligrams per square centimeter, after which the aluminized surface can be leached in hot 20% aqueous NaOH to reduce the pick-up to about 1.1 milligrams per square centimeter. This leaves a stainless steel workpiece with a very active surface highly suited for a water-electrolyzing electrode, anode or cathode, with reduced over-voltage. It is also suitable for use as a fuel cell electrode, both anode and cathode. The active nickel surface becomes warm when first exposed to air, showing that it is pyrophorically reacting with the air. Its best cathodic electrolyzing effects are provided if kept from exposure to air or oxygen. These results are also obtained when the aluminizing is conducted at other temperatures and for other times and with other diffusion-coating packs. Similarly, the nickel platings can be deposited by ion bombardment, gas plating or other techniques, and the stainless steel can be of any other type. The stainless steel support need not be more than about 10 mils thick, and can be a foil or screen.

The high diffusion temperatures suggested in U.S. Pat. No. 4,116,804 are not desirable for aluminizing a stainless steel supported thin nickel or iron layer, inasmuch as high diffusion temperatures tend to cause some of the chromium from the stainless steel to diffuse into the thin nickel or iron layer and lower its activity for electrolytic use. It is accordingly desirable to keep the diffusion temperature below 1100° F. and to limit the dwell time at diffusion temperature to prevent chromium from reaching the outer surface of the nickel or iron coating.

The nickel or iron top coating can be given a top flash plating of silver or platinum about 0.05 mil to about 0.5 mil thick, before the aluminizing. Such a flash coat of nickel over an iron-plated stainless steel is also helpful.

Similar flash coatings can be applied over the activated nickel or iron plated stainless steels after the activation is completed by aluminizing and leaching.

Even without the stainless steel backings, a self-supporting iron or nickel screen or foil having its surfaces activated as noted, with or without the flash top coatings, make very good fuel cell electrodes, much like the similar activated metals of British Specification No. 1,289,751.

A stainless steel backed activated nickel or iron plating also makes a good catalyst for NOX reduction as described in the above-noted Patent Application Ser. No. 302,979, particularly if the diffusion step has caused some of the chromium from the stainless steel to reach the surface of the plating.

The activation of an aluminized nickel surface by leaching with caustic, yields greater degrees of activity when the leaching is more vigorous. Thus, a nickel screen made of wires about 20 mils thick, after aluminizing at 850° F. for twelve hours can be leached for 1½ hours with a boiling solution of 200 grams NaOH in enough water to make 500 cc, to leave the nickel surface substantially more active than when leached for prolonged periods with 20% aqueous NaOH solution at 180° F.

Inasmuch as the initial action of the hot stronger caustic which boils at about 250° F. is very violent, the stronger caustic treatment can be started at lower temperatures such as room temperature, or can be preceded by a treatment with milder caustic. For example, a one-hour treatment with boiling 40% aqueous NaOH can be preceded by a one-hour treatment with 20% aqueous NaOH at 180° F.

Even better results are obtained by a final leaching in boiling 60% aqueous NaOH for one hour. KOH can be substitute for some or all of the NaOH in any of the leachings without significantly affecting the resulting activation.

When electrolyzing water in which an alkali like NaOH is dissolved to increase its conductivity, a nickel anode previously activated by aluminizing to give a 2-mil thick case followed by a one-hour treatment in boiling 60% or 70% NaOH, provides a much greater anodic current density than a corresponding anode in which the leaching was only with hot 20% aqueous caustic Indeed, at low inter-electrode voltages as against an untreated pure nickel cathode, the anodic current density is increased as much as seven-fold. The foregoing anodes are preferably dipped into dilute hydrogen peroxide after the leach is completed, with or without an intervening rinse in hot or boiling water.

A somewhat smaller but still spectacular current density increase is obtained from boiling 40% aqueous NaOH leach for one hour.

In general the leaches with 50% or stronger caustic should not be extended so as to remove much of the aluminum at the interface between the aluminized case and the nickel core under it. Too much removal at that location can reduce the adhesion between the core and the leached case and cause the leached case to spall off. A one-third hour leach at about 200° F. is appropriate for cases as thin as 0.5 mil, but boiling 70% caustic should not be used for more than about 10 minutes unless the case is thicker than two mils. Preferred leaching is with about 30% to about 60% aqueous NaOH at temperatures from about 212° F. to about 300° F. for at least a half-hour, but not long enough to loosen the leached layer.

The foregoing vigorous leachings also improve the cathodic current density when the leached nickel electrodes are used as cathodes, but here the current density increases are only effected at inter-electrode potentials greater than about 1.5 volts.

A 1.5 to 2 mil aluminized case applied on 430 stainless steel by powder pack diffusion below 1000° F. is preferably leached for not over about 1-¾ hours when the leaching is effected at about 150 to about 190° F. with 10% to 30% caustic. Most preferably such leaching is for about 1 to about 1½ hours, particularly for use as an NOX-reducing catalyst with $NH_3$ in furnace and internal combustion engine exhausts. Thinner cases should be leached for proportional times. Leaching at lower temperatures, e.g., at 90° F., can be extended to about 3 hours.

When leached aluminized stainless steel screening is used for NOX removal, better results are obtained with the great degree of leaching, but the aluminized case should not be completely leached through. Some of the activated stainless steel stratum may slough off during the leaching, but this does not detract materially from the NOX-reducing effectiveness so long as the case is not completely leached through.

As noted above, the leaching of aluminized ferrous metal is greatly benefitted by the presence of dissolved tin in the leaching liquor. Such leaching builds up a tin-containing sludge that can be treated to recover and re-use the tin values. To this end the sludge can be filtered off or separated by centrifugation, and washed, as in a perforated barrel washer to carry off most of the adhering caustic liquor. The washed material is then dipped in aqueous acid such, as 1:1 dilution of concentrated HCl with water, to bring it to approximate neutrality or slightly acid. A pH of about 3 to about 9 is appropriate.

The approximately neutralized material is then retorted at a temperature of about 275° to about 375° C. in a non-oxidizing atmosphere for about 5 to about 10 hours. The resulting material analyzes to about 70% tin and is completely soluble in strong HCl or other acid. It can be used as a general source of tin, for example by dissolving it in concentrated HCl warmed to at least about 60° C. to yield a stannous chloride solution that can be added to the caustic leach for the leaching of aluminized ferrous metal.

The retorting is the key treatment, inasmuch as without the retorting the sludge will not properly dissolve in the strong acid. Hydrogen or inert gas atmospheres such as argon can be used in the retorting. A 10-centimeter tall retort works satisfactorily in that only about 5 retort hours is then needed. Excess retorting does not help or hurt.

The leaching of aluminized iron foils or powder is improved when conducted with a little hydrogen peroxide in the leaching liquid. As little as 0.1% $H_2O_2$ by weight of the leachant is enough to show such results, and from about 0.2% to about 0.5% is preferred. Concentrations of 3% or higher tend to darken the work and diminish its pyrophoric activity.

By way of example, to a liter of 10 weight percent solution of NaOH in water there is added 5 grams of $SnCl_2$ $2H_2O$ and 5cc of 30% aqueous $H_2O_2$, and the resulting mixture at room temperature is used to leach 2 mil thick iron foil that has been aluminized to a depth of ½ mil on both its faces. The leaching generates a very small amount of gas as compared to corresponding leaching without the $H_2O_2$, and is completed in about 30 minutes even if the leach solution warms up to about 50° C. during the leaching. Essentially no sludge precipitates from the leach solution, even though a large quantity of tin-containing sludge precipitates if the $H_2O_2$ is omitted.

About the same results are obtained when the leachant is KOH and starting leach solution is at any temperature from about zero to about 50° C., although leachant that starts at 50° C. can heat up to about 60° C. The foregoing leachings are conducted with about one hundred times as much leach solution as substrate being leached, by weight. Preferred caustic concentrations are from about 8% to about 20% NaOH of KOH in water, by weight.

Instead of pouring $H_2O_2$ into a leach solution, peroxides such as sodium peroxide, potassium peroxide and calcium peroxide can be added to the leach solution to form $H_2O_2$ in situ.

The foil activated in accordance with the foregoing example also shows a small gain in pyrophoric heat output as compared to the corresponding foil activated without the help of the $H_2O_2$. Iron powders also give about the same results as the foils do.

Leaching of aluminized iron, either foil or powder, is best conducted with some tin or stannite ion dissolved in the leachant, but the concentration of the tin can be reduced to as little as about ½ gram dissolved tin per liter of leachant when the $H_2O_2$ of the present invention is present in the leachant. Preferably the dissolved tin content is as high as 1 to 3 grams per liter. Such tin reduction is also noted in the rapid high-temperature leaching of parent Ser. No. 707,656.

Not only is less tin needed in the leachant, but the iron activated with the $H_2O_2$ in the leachant contains less tin than is contained in iron activated pursuant to the prior art. Such tin is introduced as metal into the pores of the activated iron and even in very small amounts helps preserve the activation.

It is noted that the presence of the $H_2O_2$ in the leachant according to the present invention, has an effect opposite to that of the $H_2O_2$ when it is applied to the activated metal after the leaching is completed. Such later application causes the activated metal to lose some or all of its pyrophoricity, and to turn black.

The small increase in heat output caused by the presence of the $H_2O_2$ in the leachant, can be heightened by subsequently subjecting the activated metal to the short treatment with dilute acid, with or without the folding, as described above.

The foregoing leaching, with or without the $H_2O_2$, is also very effective for leaching the rapidly formed sintered aluminum alloys of parent Ser. No. 205,387. Those alloys are of the Raney type formed by placing the alloy precursor metals on a carrier and then rapidly heating the combination to a temperature high enough to trigger the inter-reaction of the precursor metals.

A particularly desirable technique uses as a carrier inexpensive steel such as type 1010, in the form of a foil about 25 to 50 microns thick. Such a foil can be seriously embrittled by the inter-reacting metals at the high inter-reaction temperatures generated, and to avoid excessive damage, the precursor metals are applied in at least two stages, with the first stage arranged to generate relatively low inter-reaction temperatures. Thus the atomic proportion of the aluminum to the iron, nickel or cobalt precursors should be no greater than about 2, or the metal alloying with the aluminum should be mostly iron, or the precursors can be diluted with preformed alloy, or combinations of these techniques used. One desirable arrangement uses as a first stage a mixture of:

50 grams iron powder
68.4 grams aluminum powder
14.8 grams nickel powder

This mixture can be poured onto the steel foil in a layer about 75 microns thick, or suspended in a binder solution that is applied to the foil or into which the foil is dipped. A typical binder solution is a 6% solution of polyethylacrylate in methyl chloroform. The dried combination is then heated to about 700° C., setting off the reaction between the aluminum and the other metals. After about seven seconds the reaction is completed and the alloy particles formed are sintered to each other and to the foil, with the thus-coated foil retaining some of its malleability. It can for example be bent at least about 20 degrees around a mandrel 3 centimeters in diameter.

Over the reacted coating there is then applied another precursor layer, this time a mixture of 108.8 grams aluminum
51.2 grams nickel
40 grams preformed $NiAl_2$
2 grams boron and the heat treatment repeated. The resulting coated foil can still be bent at least about 20 degrees around a mandrel 3 centimeters in diameter.

The final product, where both the precursor layers are about equal in thickness, is essentially a mixture of iron and nickel trialuminides, with a very small content of boron, sintered to aluminized iron foil. It is noted that when the precursor layers are applied by dipping, the resulting coatings are on both faces of the foil. Either way, the aluminide-coated foil is still strong enough to hold itself together and hold the aluminide particles in place. It is now leached as for example in 10% aqueous NaOH at 50 to 65° C. for two to thirty minutes, preferably with tin dissolved in the leachant.

After rinsing, the leached product can be compacted between compacting rolls, and will then be about 125 to 200 microns thick. It is highly pyrophoric and for maximum pyrophoric heat output, the heat treatments are conducted in a protective atmosphere. Conducting them in air for a total time less than about 30 seconds does not materially detract from the pyrophoric heat output. It will be noted that the reacted precursor metals as well as the carrier foil are rendered pyrophoric by the leaching.

The pyrophoric material should be kept away from oxygen, as by being thoroughly wet with water or other protective liquid, to preserve it against changes. It can be cut to short lengths for loading into a decoy shell used for protecting aircraft against heat-seeking missiles. It can also be stabilized by contacting it with very low concentrations of oxygen, as described in parent Ser. No. 685,910, to render it non-pyrophoric unless heated to above 50° C.

Obviously, many modifications and variations of the present invention are possible in the light of the above teachings. It is, therefore, to be understood that within the scope of the appended claims the invention may be practiced otherwise than as specifically described.

What is claimed:

1. In the re-use of a used jet engine hot section airfoil that had been aluminized, the improvement according to which the used airfoil is cleaned of accumulations resulting from its use, and the cleaned airfoil is subjected to fluoridizing at a temperature at least aS high as about 1650° F. to remove the aluminum remaining from the original aluminizing and deoxidized the airfoil surface, and then the de-aluminized de-oxidized surface is re-aluminized.

2. The combination of claim 1 in which the airfoil is a nickel-base superalloy and the fluoridizing treatment is conducted at a temperature no higher than about 1750° F.

* * * * *